United States Patent [19]

Motono

[11] Patent Number: 4,946,472
[45] Date of Patent: Aug. 7, 1990

[54] HAIR-DYEING COMPOSITION AND HAIR-DYEING METHOD USING THE SAME

[75] Inventor: Masahiro Motono, Kurume, Japan

[73] Assignees: Sansho Seiyaku Co., Ltd., Onojo; Teruaki Hayashi, Kawanishi, both of Japan

[21] Appl. No.: 319,584

[22] Filed: Mar. 6, 1989

[30] Foreign Application Priority Data

Mar. 18, 1988 [JP] Japan ................... 63-66854

[51] Int. Cl.$^5$ .......................... A61K 7/13; C09B 67/00
[52] U.S. Cl. .......................................... 8/424; 8/405; 8/429; 8/623; 8/432
[58] Field of Search ................... 8/424, 405, 406, 429, 8/423; 560/68; 424/647, 648; 514/533

[56] References Cited

U.S. PATENT DOCUMENTS

| | | | |
|---|---|---|---|
| 4,517,175 | 5/1985 | Iwabuchi et al. | 424/70 |
| 4,530,829 | 7/1985 | Abe | 424/70 |

FOREIGN PATENT DOCUMENTS

| | | |
|---|---|---|
| 297547 | 1/1989 | European Pat. Off. |
| 53-72836 | 6/1978 | Japan . |
| 60-048916 | 3/1985 | Japan . |
| 62-132813 | 6/1987 | Japan . |
| 63-041414 | 2/1988 | Japan . |

OTHER PUBLICATIONS

Fukaya et al., "Effect of Tannin on Oxidative Damage of Ocular Lens", 1988, Jpn. J. Ophthamol., 32(2), 166–75 (Abstract).

Fukuchi et al., "Inhibition of Herpes Simplex Virus Infection by Tannins and Related Compounds", Antiviral Res., 11(5–6), 285–97, 1989 (AB).

*Primary Examiner*—Paul Lieberman
*Assistant Examiner*—James M. Silbermann
*Attorney, Agent, or Firm*—Jordan and Hamburg

[57] ABSTRACT

Disclosed is a hair-dyeing composition comprising geraniintannin and a water-soluble iron salt and optionally containing one or more selected from tannic acid, L-cysteine and salts thereof, sodium hydrogen sulfite, sodium sulfite, hydrolyzed product of collagen and resins for hair. The composition may be in the form of either a one-solution-type or a two-solution-type. Also disclosed is a hair-dyeing method using the said composition. The hair dyed with the composition has an almost natural and fast black color.

10 Claims, No Drawings

HAIR-DYEING COMPOSITION AND HAIR-DYEING METHOD USING THE SAME

BACKGROUND ON THE INVENTION

1. Field of the Invention

The present invention relates to a hair-dyeing composition which comprises geraniintannin and a water-soluble iron salt and which has excellent black colorability, dyeability, color tone and color fastness, as well as to a hair-dyeing method using the same.

2. Prior Art

In general, a so-called gray-hair-dyeing composition for dyeing the gray hair of the aged is widely used. The gray-hair-dyeing composition which is generally used at present is essentially an oxidizing hair-dyeing composition. The hair-dyeing composition of this kind comprises a dye intermediate of an aromatic amino compound such as paraphenylenediamine, a coupler of a phenol compound such as m-phenylenediamine or m-aminophenol, and an oxidizing agent such as hydrogen peroxide or sodium perborate.

However, such a hair-dyeing composition has a drawback as a substance which is directly applied to the skin, as the dye intermediate component in the composition causes inflammation of the skin. In addition, the operation for dyeing hair with the composition is complicated since plural agents of the dye intermediate, coupler and oxidizing agent are to be used.

In order to overcome inflammation or any similar disorder of the skin by the said oxidizing hair-dyeing composition, a non-oxidizing type hair-dyeing composition has been proposed, which comprises a water-soluble iron salt and gallic acid, tannic aid and pyrogallol. (For example, refer to Japanese Patent Kokai Nos. 49-36838, 60-209513 and 51-56119.)

In addition, a hair-dyeing composition of another type is also known, which comprises Japanese gall, nutgall (Turkey gall) extract and ferric chloride (Japanese Patent Kokai No. 62-116504).

The non-oxidizing type hair-dyeing compositions by the prior art have defective problems in that the dyeability thereof is poor, the hair blackened therewith does not have a glossy and lustrous color tone which is intrinsic t black hair and the blackened hair is faded by shampoo and is lacking in color fastness.

SUMMARY OF THE INVENTION

The object of the present invention is to provide a non-oxidizing type hair-dyeing composition which can dye gray hair into black hair having a nearly natural color tone and having a high color fastness, as well as a hair-dyeing method using the said hair-dyeing composition.

In order to attain the said object, there is provided, in accordance with the present invention, a hair-dyeing composition comprising geraniintannin and a water-soluble iron salt. As one embodiment of the present invention, the composition is a one-solution-type hair-dyeing composition comprising geraniintannin and a water-soluble iron salt as a mixture thereof.

As another embodiment of the present invention, the composition is a two-solution-type hair-dyeing composition composed of a geraniintannin-containing first solution and a second solution of an aqueous water-soluble iron salt solution.

In accordance with the present invention, there is also provided a hair-dyeing method with the said hair-dyeing composition, where the geraniintannin-containing first solution is first applied to the hair to be blackened and, after the hair is dried, the second solution of the aqueous water-soluble iron salt-containing solution is thereafter applied to the hair.

DETAILED DESCRIPTION OF THE INVENTION

The present inventor has noted the fact that the reaction of a tannin and an iron salt yields a black color and he carried out various hair dyeing tests for various tannins with such knowledge. As a result, it has been found that geraniintannin is superior to any other tannins such as catechin-tannin and tannic acid since the former has a higher coloring capacity for dyeing a gray hair into a nearly natural black-colored hair than the latter, and thus the present invention has been completed.

In addition, it has also been found that incorporation of one or more selected from tannin acid, L-cysteine and salts thereof, sodium hydrogen sulfite, sodium sulfite, hydrolyzed product of collagen and resins for hair into the hair-dyeing composition of the invention is advantageous for increasing the color fastness of the hair as blackened with the composition.

Accordingly, the present invention provides a hair-dyeing composition comprising geraniintannin and a water-soluble iron salt; a hair-dyeing composition additionally containing one of more selected from tannic acid, L-cysteine and salts thereof, sodium hydrogen sulfite, sodium sulfite, hydrolyzed product of collagen and resins for hair, in addition to geraniintannin and water-soluble iron salt; a one-solution-type hair-dyeing composition comprising geraniintannin and a water-soluble iron salt as a mixture; a two-solution-type hair-dyeing composition composed of a geraniintannin-containing solution and an aqueous water-soluble iron salt solution; and a hair-dyeing method with the said hair-dyeing composition where the first solution of the geraniintannin-containing solution is first applied to a hair and, after dried, the second solution of the aqueous water-soluble iron salt solution is then applied to the hair.

In general, it is said that tannins have an astringent effect to the skin and mucosa. Because of the effect, tannins have widely been utilized as a tanning agent, an antidiarrheal and an antiinflammatory agent from the past. Geraniintannin is well known as the main ingredient of a herb cranesbill (*Geranium nepalense var. thunbergii*). Geraniintannin is known as a tannin which does not taste bitter, although it has a strong biding capacity with proteins. It is said that geraniintannin is a tannin which hardly stimulates the skin and mucosa.

Geraniintannin is derived form a herb cranesbill. A powdered form of the herb is extracted with a mixed solvent of ether/water (3/1), and the ether layer is harvested. This is concentrated under reduced pressure and ethanol is added thereto. The resulting mixture is discolored, filtered and further concentrated under reduced pressure. The concentrated liquid is dried to obtain a powder. The powder thus obtained contains geraniintannin in an amount of about 90%.

As the water-soluble iron salt for use in the present invention may be any iron salt which is soluble in water and may react with a tannin to be colored in black, for example, ferric chloride, ferrous chloride, ferric sulfite or ferric phosphate. Among these, ferric chloride is preferred.

The hair-dyeing composition of the present invention comprises the above-mentioned geraniintannin and water-soluble iron salt. The composition may be in any form of one-solution-type and two-solution-type compositions, which may properly be selected in accordance with the use of the composition.

In the case of a one-solution-type composition, it is an aqueous solution containing the said geraniintannin in an amount of from 0.1 to 10.0% by weight, preferably from 1.0 to 5.0% by weight, and the said water-soluble iron salt in an amount of from 0.01 to 5.0% by weight, preferably from 1.0 to 3.0% by weight. A polyhydric alcohol such as propylene glycol or glycerin or ethanol is added to the said aqueous solution to form a liquid, emulsion or cream, which may directly be applied to a gray hair to blacken the same. Alternatively, it may be incorporated into shampoo or rinse.

In the case of a two-solution-type composition, a polyhydric alcohol such as propylene glycol or glycerin or ethanol is added to an aqueous solution containing the above-mentioned geraniintannin in an amount of from 0.1 to 10.0% by weight, preferably from 1.0 to 5.0% by weight, to form a first solution.

One the other hand, ethanol is added to an aqueous solution containing the above-mentioned water-soluble iron salt in an amount of from 0.1 to 10% by weight, preferably from 2.0 to 5.0% by weight, to form a second solution.

Addition of one or more selected from tannic acid, L-cystein and salts thereof, sodium hydrogen sulfite, sodium sulfite, hydrolyzed product of collagen and resins for hair to the hair-dyeing compositions of the present invention is advantageous, since the hair blackened with the resulting composition may have an elevated color fastness even after repeated hair-shampooing. The resins for hair include, for example, a copolymer of ethoxyethyl acrylate and hydroxyethyl acrylate, a cationated cellulose, etc.

The amount of the said additives to be added to the composition of the invention is from 0.1 to 5.0% by weight, preferably from 0.5 to 3.0% by weight. They may be added to the mixture of geraniintannin and water-soluble iron salt for the one-solution-type composition, or may be added to the geraniintannin-containing solution for the two-solution-type composition.

In the case of the two-solution-type composition, the first solution is first applied to hair and kept as it is until the solution becomes dried, or the hair is dried with a drier, and the second solution is then applied to the hair.

Next, the following examples illustrate some embodiments of the hair-dyeing composition of the present invention and the hair-dyeing method using the composition, which, however, do not whatsoever restrict the scope of the present invention.

EXAMPLE 1

Two-solution-type Composition:

1.0% of geraniintannin, 1.0% of tannin acid, 5.0% of propylene glycol, 5.0% of ethanol (95%), 1.2% of carboxyvinyl polymer, 0.5% of L-cysteine hydrochloride and 86.3% of pure water were mixed to form a first solution.

5.0% of ferric chloride, 40.0% of ethanol and 55.0% of pure water were mixed to form a second solution. (The "percentage" is all by weight.)

EXAMPLE 2

One-solution-type Composition:

1.0% of geraniintannin, 1.0% of tannic acid, 5.0% of propylene glycol, 30.0% of ethanol, 1.0% of ferric chloride, 0.5% of sodium hydrogen sulfite and 61.5% of pure water were mixed to form a hair dyeing composition. (The "percentage" is all by weight.)

EXAMPLE 3

Hair-dyeing method with the Hair-dyeing Composition of the Invention:

The two-soluble-type composition prepared in Example 1 was used for dyeing a gray hair. A proper amount of the first solution was applied to the necessary part of the gray hair to be blackened with a comb. During application of the composition to the hair, the hair was dried with a drier. Then the hair was kept as it was for a while, and thereafter the second solution was lightly sprayed over the hair, whereupon the hair was colored in a dark black and the hair was combed to complete the hair-dyeing.

EXPERIMENTAL EXAMPLE 1

Comparative Test for Coloration and Color Tone Using Various Tannins and Iron Salts:

(a) Samples:
(1) Solution comprising 1.0% of geraniintannin, 10.0% of propylene glycol, 10.0% of ethanol and 79.0% of pure water.
(2) Solution comprising 1.0% of catechin-tannin, 10.0% of propylene glycol, 10.0% of ethanol and 79.0% of pure water.
(3) Solution comprising 0.6% of geraniintannin, 0.4% of tannic acid, 10.0% of propylene glycol, 10.0% of ethanol and 79.0% of pure water.
(The "percentage" is all by weight.)

(b) Test Method:
1 ml of each of Samples (1) to (3) and 1 ml of aqueous solution of 0.1M ferric chloride or ferrous chloride were mixed, and the color of the resulting mixture was observed with the naked eye immediately after preparation of the mixture and one day after the said preparation.

(c) Test Result:
The results are shown in Table 1.

TABLE 1

| Sample | Fresh | One-day Stored |
|---|---|---|
| (1) & Ferric Chloride | Black (A) | Somewhat Greenish Black (B) |
| (2) & Ferric Chloride | Black (B) | Blackish Brown |
| (3) & Ferric Chloride | Dark Black (A) | Dark Black (A) |
| (1) & Ferrous Chloride | Greenish Black (B) | Black (C) |
| (2) & Ferrous Chloride | Green (D) | Blackish Green (B) |
| (3) & Ferrous Chloride | Black (A) | Black (A) |

Note:
A ... Excellent
B ... Very Good
C ... Good
D ... Somewhat Good

From the results shown in Table 1, it noted that geraniintannin is better than catechin-tannin as the former had a higher reactivity and gave a darker black color than the latter in the coloration test (in vitro) using a tannin-containing solution and an iron salt solution.

Addition of the tannic acid to geraniintannin resulted in increase of the black density of the color formed.

EXPERIMENTAL EXAMPLE 2

Comparative Test for Coloration and Color Tone Using Various L-cysteine Hydrochloride-containing Tannins and Iron Salts:

(a) Samples:
(1) Solution comprising 1.0% of geraniintannin, 0.5% of L-cysteine hydrochloride, 10.0% of propylene glycol, 10.0% of ethanol and 78.5% of pure water.
(2) Solution comprising 1.0% of geraniintannin, 0.05% of L-cysteine hydrochloride, 10.0% of propylene glycol, 10.0% of ethanol and 78.95% of pure water.
(3) Solution comprising 1.0% of tannic acid, 0.5% of L-cysteine hydrochloride, 10.0% of propylene glycol, 10.0% of ethanol and 78.5% of pure water.
(4) Solution comprising 1.0% of tannic acid, 0.05% of L-cysteine hydrochloride, 10.0% of propylene glycol, 10.0% of ethanol and 78.95% of pure water.
(5) Solution comprising 1.0% of catechin-tannin, 0.5% of L-cysteine hydrochloride, 10.0% of propylene glycol, 10.0% of ethanol and 78.5% of pure water.
(6) Solution comprising 1.0% of catechin-tannin, 0.05% of L-cysteine hydrochloride, 10.0% of propylene glycol, 10.0% of ethanol and 78.95% of pure water.
(The "percentage" is all by weight.)

(b) Test Method:
1 ml of each of Samples (1) to (6) and 1 ml of aqueous solution of 0.1M ferric chloride were mixed, and the color of the resulting mixture was observed with the naked eye immediately to 30 minutes after preparation of the mixture and two days after the said preparation.

(c) Test Result:
The results are shown in Table 2.

TABLE 2

| Sample | Fresh to 30-minute Stored | 2-day Stored |
|---|---|---|
| (1) | Dark Black (A) | Dark Blackish Green (A) |
| (2) | Black(A) | Dark Green(D) |
| (3) | Black(B) | Blackish Brown (A) |
| (4) | Somewhat Greenish Black (B) | Dark Green (D) |
| (5) | Black Olive Brown maroon (B) | Dark Reddish Brown (B) |
| (6) | Blackish Brown Olive Brown | Reddish Wine (B) |

Note:
A, B, C, D . . . Same as those in Table 1.

Addition of 0.5% of L-cysteine hydrochloride to 1% of tannin prevents formation of a precipiate from tannin and iron salt, whereby the composition may be stabilized and the color-absorbability to hair is improved.

EXPERIMENTAL EXAMPLE 3

DDY Mouse Hair-Dyeing Test Using Various Tannins and Iron Salts:

(a) Samples:
A liquid comprising 5.0% of ethanol, 5.0% of propylene glycol and 0.8% of carboxyvinyl polymer was used as a base material. To the base material, 2.0% of geraniintannin was added to form Sample (1), 2.0% of catechin-tannin was added to form Sample (2). 2.0% of tannic acid was added to form Sample (3), and 1.0% of geraniintannin and 1.0% of tannic acid were added to form Sample (4). To each sample was added pure water, and the resulting mixture was gelled with potassium carbonate. The gel was subjected to the following hair-dyeing test.

(b) Test Method:
1 ml of each of Samples (1) to (4) was applied to the hair of the back of a DDY mouse (male 7 to 1-week age). After left as it was for about 5 minutes, the hair was dried with a drier. Next, about 1 ml of aqueous 5.0% ferric chloride solution was applied to the same part of the back, and the coloration and hue (colorability) as well as the color of the dyed hair (dyeability) were observed with the naked eye. (The "percentage" is all bye weight.)

(c) Test Result:
The test results are shown in Table 3.

TABLE 3

| Sample | Coloration, Hue (Colorability) | Color of Dyed Hair |
|---|---|---|
| (1) | Black (A) | Grayish Black (B) |
| (2) | Greenish Black (B) | Light Gray (D) |
| (3) | Blueish Black (B) | Grayish Black (C) |
| (4) | Dark Black (A) | Black (A) |

Note:
A, B, C, D . . . Same as those in Table 1.

From the results shown in Table 3, it is noted that geraniintannin had a good dyeability, and the hair was dyed best in black by the use of the combination of geraniintannin and tannic acid. The dyeability was improved by drying the hair after the tannin-containing solution was applied to the hair.

EXPERIMENTAL EXAMPLE 4

Color Fastness Test:

About 1 ml of a solution (first solution) comprising 0.1% of geraniintannin, 1.0% of tannic acid, 5.0% of ethanol, 5.0% of propylene glycol, 5.0% of L-cysteine hydrochloride and 87.5% of pure water was applied to the gray hair of the back of a DDY mouse (male, 7 to 10-week age). After left as it was for about 5 minutes, the hair was dried with a hot air from a drier, and about 1 ml of aqueous 5% ferric chloride solution (second solution) was applied to the hair, which was then colored in a greenish dark black. (The "percentage" is all by weight.)

After thus dyed, the hair was washed with tepid water. The thus washed hair was observed to be colored dark black. Next, the thus dyed hair was shampooed and the hair was observed to remain black.

From the said result, it is noted that the hair-dyeing composition comprising geraniintannin and ferric chloride may dye the hair in a fast black color and the thus dyed hair is not faded but can keep the originally dyed color even after washing with a tepid water or after shampooing.

The present invention provides a safe non-oxidizing hair-dyeing composition which does not damage the skin. When dyed with the composition, the hair may be colored in a nearly natural black color, and the thus dyed hair is not faded even after shampooing. The present invention also provides a hair-dyeing method with the said hair-dyeing composition. The hair dyed by the method using the hair-dyeing composition of this invention may be colored in a fast black color. The present invention is therefore an extremely useful invention.

While the invention has been described in detail and with reference to specific embodiments thereof, it will be apparent to one skilled in the art that various changes and modifications can be made therein without departing from the spirit and scope thereof.

What is claimed is:

1. A hair-dyeing composition comprising geraniintannin and a water-soluble iron salt.

2. A hair-dyeing composition comprising geraniintannin and a water-soluble iron salt and additionally one or more compounds selected from tannic acid, L-cysteine and salts thereof, sodium hydrogen sulfite, sodium sulfite, hydrolyzed product of collagen and resins for hair.

3. A one-solution-type hair-dyeing composition comprising geraniintannin and a water-soluble iron salt as a mixture thereof.

4. A one-solution-type hair-dyeing composition comprising geraniintannin and a water soluble iron salt as a mixture thereof and additionally containing one or more compounds selected from tannic acid, L-cysteine and salts thereof, sodium hydrogen sulfite, sodium sulfite, hydrolyzed product of collagen and resins for hair.

5. A two-solution-type hair-dyeing composition composed of a geraniintannin-containing first solution and a second solution of an aqueous water-soluble iron salt.

6. A two-solution-type hair-dyeing composition composed of a first solution comprising geraniintannin and one or more compounds selected from tannic acid, L-cysteine and salts thereof, sodium hydrogen sulfite, sodium sulfite, hydrolyzed product of collagen and resins for hair and a second solution of an aqueous water-soluble iron salt solution.

7. The hair-dyeing composition as claimed in anyone of claims 1 to 6, in which the water-soluble iron salt is ferric chloride.

8. A hair-dyeing method comprising applying a first solution of a geraniintannin-containing solution to hair, drying the hair and applying a second solution of an aqueous water-soluble iron salt solution to the hair.

9. A hair-dyeing method comprising applying a first solution composed of a geraniintannin-containing solution and one or more compounds selected from tannic acid, L-cysteine and salts thereof, sodium hydrogen sulfite, sodium sulfite, hydrolyzed product of collagen and resin for hair to hair, drying the hair and applying a second solution of an aqueous water-soluble iron salt solution to the hair.

10. The hair-dyeing method as claimed in claim 9, in which the water-soluble iron salt is ferric chloride.

* * * * *